United States Patent
Di Santo et al.

(10) Patent No.: US 9,439,404 B2
(45) Date of Patent: Sep. 13, 2016

(54) BOOSTING HUMAN DENDRITIC CELL DEVELOPMENT, HOMEOSTASIS AND FUNCTION IN XENOGRAFTED IMMUNODEFICIENT MICE

(71) Applicants: INSERM (Institut National de la Santé et de la Recherche Médicale), Paris (FR); INSTITUT PASTEUR, Paris (FR)

(72) Inventors: James Di Santo, Paris (FR); Jean-Jacques Mention, Paris (FR)

(73) Assignees: INSERM (Institut National de la Santé et de la Recherche Médicale), Paris (FR); INSTITUT PASTEUR, Paris (FR)

( * ) Notice: Subject to any disclaimer, the term of this patent is extended or adjusted under 35 U.S.C. 154(b) by 0 days.

(21) Appl. No.: 14/182,773

(22) Filed: Feb. 18, 2014

(65) Prior Publication Data
US 2014/0165220 A1    Jun. 12, 2014

Related U.S. Application Data

(62) Division of application No. 13/262,567, filed as application No. PCT/US2010/029800 on Apr. 2, 2010, now abandoned.

(60) Provisional application No. 61/166,697, filed on Apr. 3, 2009.

(51) Int. Cl.
*A01K 67/027* (2006.01)
*C12N 15/85* (2006.01)

(52) U.S. Cl.
CPC ....... *A01K 67/0271* (2013.01); *A01K 67/0275* (2013.01); *C12N 15/8509* (2013.01); *A01K 2207/15* (2013.01); *A01K 2217/075* (2013.01); *A01K 2217/15* (2013.01); *A01K 2227/105* (2013.01); *A01K 2267/02* (2013.01); *A01K 2267/03* (2013.01)

(58) Field of Classification Search
CPC ............ A01K 67/0271; A01K 67/0275; A01K 2207/15; A01K 2217/15; A01K 2227/105; A01K 2267/03; C12N 15/8509
USPC ........................................ 800/9, 18
See application file for complete search history.

(56) References Cited

U.S. PATENT DOCUMENTS 4,736,866 A   4/1988 Leder et al.
4,870,009 A   9/1989 Evans et al.
4,873,191 A   10/1989 Wagner et al.

FOREIGN PATENT DOCUMENTS

WO   WO 2008/069659   * 6/2008
WO   2008/069659   12/2008

OTHER PUBLICATIONS

Karsunky et al, J. Exp. Med. 198(2):305-313, 2003.*
Mackarehtschian et al, Immunity 3:147-161, 1995.*
Maraskovsky et al, J. Exp. Med. 184(5):1953-1962, 1996.*
Brasel et al, Blood 96(9): 3029-3039, 2000.*
Bjorck, Blood 98(13):3520-3526, 2001.*
Brehm, M. et al., "Parameters for establishing humanized mouse models to study human immunity: analysis of human hematopoietic stem cell engraftment in three immunodeficient strains of mice bearing the IL2rgamma(null) mutation", Clin. Immunol. (2010), vol. 135, pp. 84-98.
Cheng, M. et al., "Distinct and overlapping patters of cytokine regulation of thymic and bone marrow-derived NK cell development", J. Immunol. (2009), vol. 182, pp. 1460-1468.
Choi, B. K. et al., "Reconstitution of human lymphocytes following ex vivo expansion of human umbilical cord blood CD34<+> cells and transplantation in rag2<-/-> gammac<-/-> mice model", Transplantation proceedings (2008), vol. 40, pp. 2655-2660.
Huntington, N. D. et al., "IL-15 trans-presentation promotes human NK cell development and differentiation in vivo", J. Exp. Med. (2009), vol. 206:1, pp. 25-34.
Huntington, N. D. et al., Humanized immune system (HIS) mice as a tool to study human NK cell development, Current Topics in Microbiology and Immunology (2008), vol. 324, pp. 109-124.
Huntington, N. D. et al., Developmental pathways that generate natural-killer-cell diversity in mice and humans, Nature (2007), vol. 7, pp. 703-714.
Joo, S.Y. et al., "Development of functional human immune system with the transplantations of human fetal liver/thymus tissues and expanded hematopoietic stem cells in RAG2<-/->gammac<-/-> mice", Transplantation Proceedings (2009), vol. 41, pp. 1885-1890.
Lan, P. et al., "Reconstitution of a functional human immune system in immunodeficient mice through combined human fetal thymus/liver and CD34+ cell transplantation", Blood (2006), vol. 108:2, pp. 487-492.
Legrand, N. et al., "Humanized mice for modelling human infectious disease: challenges, progress, and outlook", Cell Host Microbe (2009), vol. 6, pp. 5-9.
Macchiarini, F. et al., "Humanized mice: are we there yet?" J. Exp. Med. (2005), vol. 202:10, pp. 1307-1311.

(Continued)

*Primary Examiner* — Kevin Hill
(74) *Attorney, Agent, or Firm* — Kenyon & Kenyon LLP

(57) ABSTRACT

The present invention relates to a transgenic animal model system based on the development of transgenic mice bearing components of the human immune system. Specifically, the invention relates to a Flk2 deficient Rag$^{-/-}$γc$^{-/-}$ transgenic mouse and the engraftment of said mouse with human hematopoietic stem cells. The present invention further provides methods for increasing the numbers of functionally competent human dendritic cells and the hematopoietic targets cells that they interact with in said transgenic mouse through the administration of Flk2L. The transgenic animal model system of the invention may be used for testing human vaccine candidates, for screening potential immune adjuvants and for developing novel therapeutics.

10 Claims, 5 Drawing Sheets

(56) References Cited

OTHER PUBLICATIONS

Figure 2:
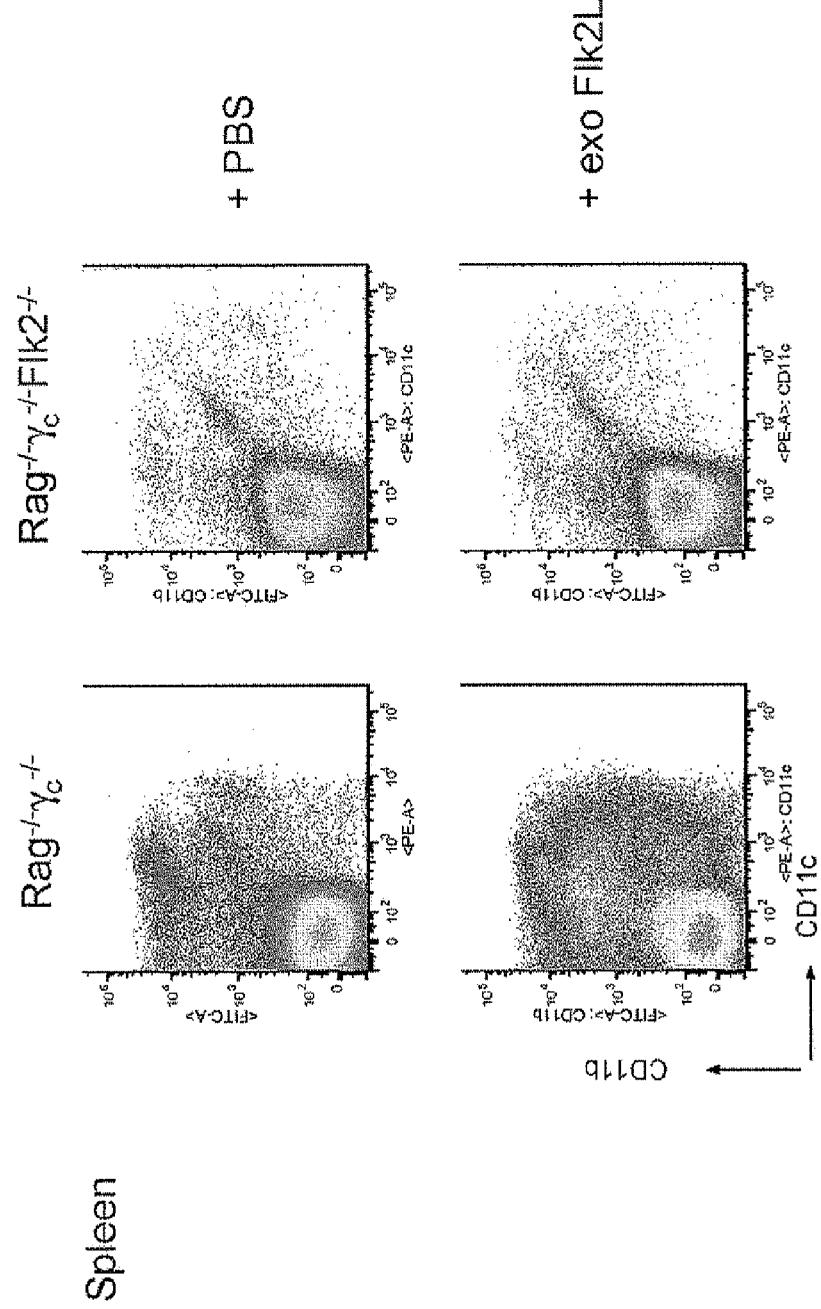

Mackarehtschian, K. et al., "Targeted disruption of the flk2/flt3 gene leads to deficiencies in primitive hematopoietic progenitors", Immunity (1995), vol. 3, pp. 147-161.

McKenna H. J., "Role of hematopoietic growth factors/flt3 ligand in expansion and regulation of dendritic cells", Current Opinion in Hematology (2001), vol. 8, pp. 149-154.

Pearson T. et al., "Non-obese diabetic-recombination activating gene-1 (NOD-Rag1 null) interleukin (IL)-2 receptor common gamma chain (IL2r gamma null) null mice: a radioresistant model for human lymphohaematopoietic engraftment" Clin. Exp. Immunol. (2008), vol. 154, pp. 270-284.

Shultz, L.D. et al., "Humanized mice in translational biomedical research", Nature (2007), vol. 7., pp. 118-130.

Traggiai, E. et al., "Development of a human adsptive immune system in cord blood cell-transplanted mice", Science (2004), vol. 304, pp. 104-107.

Vuckovic, S. et al., "Compartmentalization of allogeneic T-cell responses in the bone marrow and spleen of humanized NOD/SCID mice containing activated human resident myeloid dendritic cells", Exp. Hematology (2008), vol. 36, pp. 1502-1512.

* cited by examiner

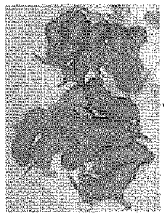
Figure 1a
Figure 1b

BOOSTING HUMAN DENDRITIC CELL DEVELOPMENT, HOMEOSTASIS AND FUNCTION IN XENOGRAFTED IMMUNODEFICIENT MICE

1. INTRODUCTION

The present invention relates to a transgenic animal model system based on the development of transgenic mice bearing components of the human immune system. Specifically, the invention relates to a Flk2 deficient $Rag^{-/-}\gamma c^{-/-}$ transgenic mouse and the engraftment of said mouse with human hematopoietic stem cells. The present invention further provides methods for increasing the numbers of functionally competent human dendritic cells and the hematopoietic targets cells that they interact with in said transgenic mouse through the administration of Flk2L. The transgenic animal model system of the invention may be used for testing human vaccine candidates, for screening potential immune adjuvants and for developing novel therapeutics.

2. BACKGROUND OF THE INVENTION

Dendritic cells (DC) derive from hematopoietic stem cells (HSC) and develop under the influence of defined growth factors. DCs have an essential role in the initiation of immune responses and in assuring peripheral immune tolerance. Still, the mechanisms that generate these biological outcomes are not known. In addition, few small animal models are currently available to study the biology of human DCs in vivo.

Human Immune System (HIS) mice harboring all three classes of human lymphocytes (B, T, NK cells) can be generated following transfer of human $CD34^+$ HSC to newborn Balb/c $Rag2^{-/-}\gamma c^{-/-}$ mice. While human DCs are observed in HIS mice, their development appears suboptimal and their homeostasis may be perturbed, possibly due to competition with endogenous mouse DCs that develop normally in these recipients. As a result, DC responses in HIS mice are primarily of mouse origin. Since human and mouse DC respond differently during immune responses, a HIS mouse model with a minimal mouse DC compartment and a maximal human DC compartment would be advantageous.

In order to address these shortcomings, the present invention provides an improved HIS mouse model that compromises endogenous mouse DC development and allows for preferential human DC development. HIS mice generated in this new recipient strain, using an exogenous cytokine boost protocol, develop human B, T, and NK cells, but show enhanced human DC development (including both classical $CD11c^+$ DCs as well as $CD123^+$ plasmacytoid DC). Moreover, increased percentages of human $CD15^+CD33^+$ myeloid cells and $CD14^+$ monocytes and macrophages could be identified in the spleen and bone marrow of transplanted mice. The human DCs identified in said HIS mice were functional, producing cytokines and soluble inflammatory factors following TLR stimulation. Increased human DC also improved the numbers of human NK and T cells in the recipient HIS mice.

3. SUMMARY OF INVENTION

The present invention relates to a transgenic animal model system comprising Flk2 deficient $Rag^{-/-}\gamma c^{-/-}$ mice. The present invention further relates to the Flk2 deficient $Rag^{-/-}\gamma c^{-/-}$ mice of the invention engrafted with human hematopoietic stem cells. The present invention further provides methods for increasing the numbers of functionally competent human dendritic cells, and the hematopoeitic target cells they interact with, through the administration of exogenous growth factors. In a specific embodiment of the invention, the exogenous growth factor is fetal liver kinase 2 ligand (Flk2L; also referred to as Flt3L). HIS mice generated using this novel approach harbor increased numbers of functional human DC, myeloid, NK and T cells and provide a novel tool to study the biology of human DCs in health and disease. Accordingly, the transgenic animal model system of the invention provides a novel means to assess in vivo the efficacy and potential drawbacks of vaccine candidates and to evaluate new adjuvants that can modify immune responses. In this way, HIS mice bearing improved numbers of functional human DCs can be used as a screening platform for immune modulators that act directly on DC or indirectly on T cells and NK cells via DC. The invention also provides a novel transgenic animal model system to investigate pathogenic immune subversion mechanisms that operate in vivo via modification of human DC function and which result in an altered, either increased or decreased, immune response against the pathogen. The invention further relates to the utilization of said model system to screen for, or identify, compounds that modulate (increase or decrease) the number and/or activity of DCs. Such compounds may be used in immunotherapies for treatment of pathogenic diseases, cancer, autoimmune, infectious and inflammatory diseases and for treatment of transplant patients.

4. BRIEF DESCRIPTION OF THE DRAWINGS

FIG. 1A-B. Flk2-deficient $Rag^{-/-}\gamma c^{-/-}$ mouse model. FIG. 1A. Critical information concerning the biological roles for the Flk2/Flt3 receptor and its ligand (Flk2L/Flt3L) as observed in $Flk2^{-/-}$ mice and mice treated with Flk2L. B) Experimental strategy used to obtain "DC-boosted" HIS mice. Recipient mice are Flk2-deficient $Rag^{-/-}\gamma c^{-/-}$ mice on the Balb/c background. Newborn recipients are injected with human $CD34^+$ hematopoietic stem cells (HSC) and subsequently treated with exogeneous Flk2L. Either mouse or human Flk2L can be used to boost human dendritic cells (DC).

FIG. 2. Reduced mouse DC in $Rag^{-/-}\gamma c^{-/-}Flk2^{-/-}$ mice. Analysis of mouse DC in spleens of adult $Rag^{-/-}\gamma c^{-/-}$ mice versus $Rag^{-/-}\gamma c^{-/-}Flk2^{-/-}$ mice that have been treated with either PBS or exogenous mouse Flk2L for two weeks. Murine $CD11b^+$ myeloid cells and $CD11c^+$ dendritic cells are reduced in PBS treated $Rag^{-/-}\gamma c^{-/-}Flk2^{-/-}$ mice compared to PBS treated $Rag^{-/-}\gamma c^{-/-}$ mice. Increased $CD11b^+$ and $CD11c^+$ cells are observed in $Rag^{-/-}\gamma c^{-/-}$ mice receiving exogenous mouse Flk2L but not in $Rag^{-/-}\gamma c^{-/-}Flk2^{-/-}$ mice. In this experiment, mouse Flk2L was provided by subcutaneous implantation of B16 melanoma cells that have been transfected with a full-length cDNA encoding mouse Flk2L. Similar results were obtained using recombinant human Flk2L-Ig fusion protein (available from BioXcell Inc.) by providing 10 ug/mouse; 3 times per week for 2 weeks.

FIG. 3A-B. More human DC develop in HIS mice made in Flk2-deficient $Rag^{-/-}\gamma c^{-/-}$ recipients. FIG. 3A. Analysis of human $CD123^+$ plasmacytoid dendritic cells (pDC) and human $CD11c^+$ conventional dendritic cells (cDC) in the spleen of HIS mice generated in $Rag^{-/-}\gamma c^{-/-}$ recipients versus $Rag^{-/-}\gamma c^{-/-}Flk2^{-/-}$ recipients that have (+ exo Flk2L) or have not received exogeneous recombinant human Flk2L (5 ug/mouse; 3 times per week for 2 weeks). Percentages of human pDC and cDC are boxed. FIG. 3B) Quantification of human DC subsets in HIS mice generated in Rag$^{-/-}$γc$^{-/-}$ recipients versus Rag$^{-/-}$γc$^{-/-}$Flk2$^{-/-}$ recipients that have (+exo Flk2L) or have not received exogenous recombinant human Flk2L (5 ug/mouse; 3 times per week for 2 weeks). Absolute numbers of spleen DC subsets and CD19$^+$ B cells are shown.

Figure 4:
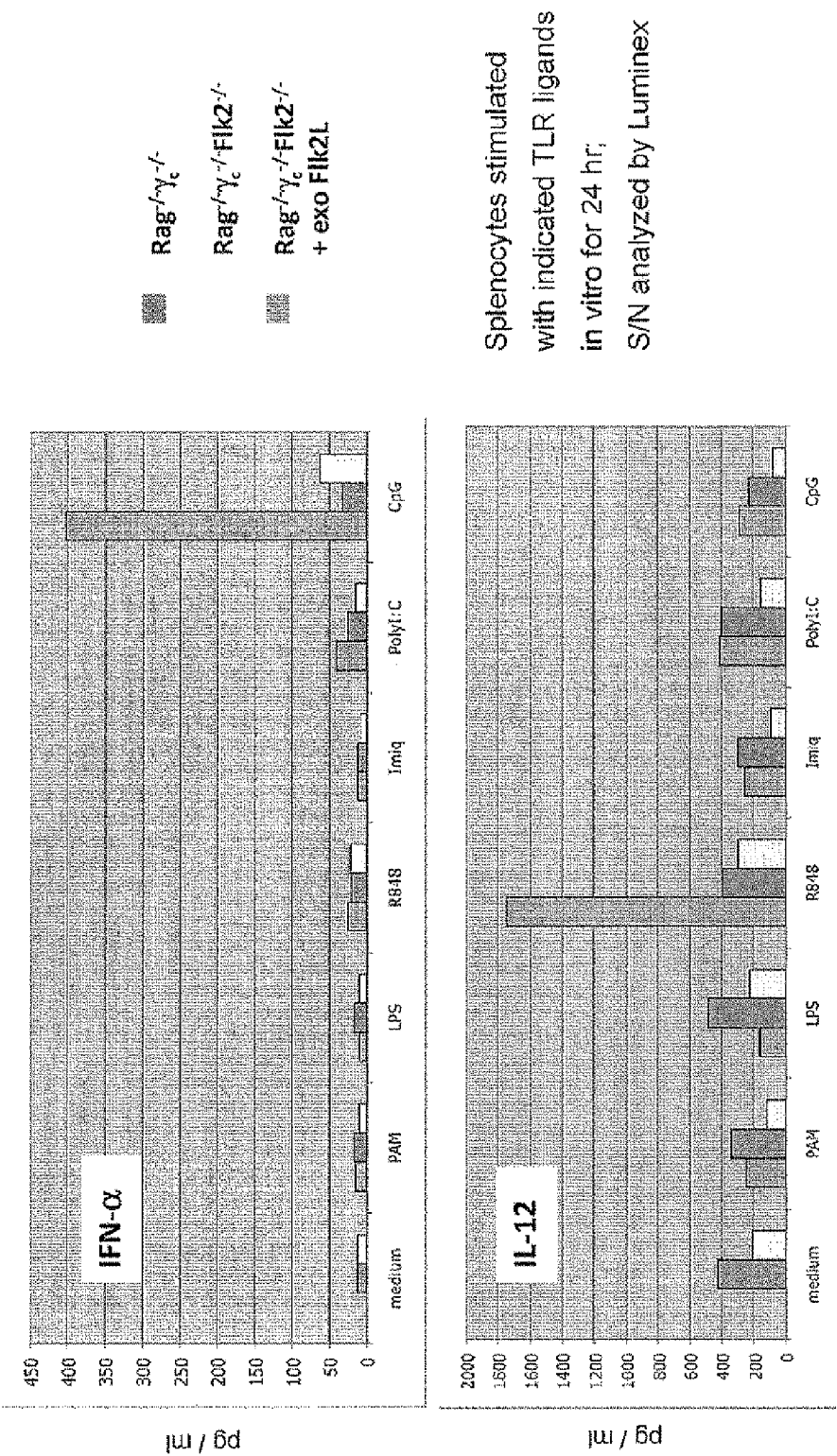

FIG. 4. Improved human DC function in "DC-boosted" HIS mice. Splenocytes from HIS mice made in the indicated recipients were isolated and cultured for 24 hours in the presence of the indicated TLR ligands (final concentration 5-20 ug/ml). Soluble factors of human origin secreted into the culture supernatant were detected and quantitated using Luminex technology. Note that human IFN-α is normally produced by pDC in response to CpG and this occurs only in DC-boosted HIS mice. Similarly, cDC produce IL-12 in response to R848 (a TLR7/8 ligand) in DC-boosted HIS mice.

Figure 5:
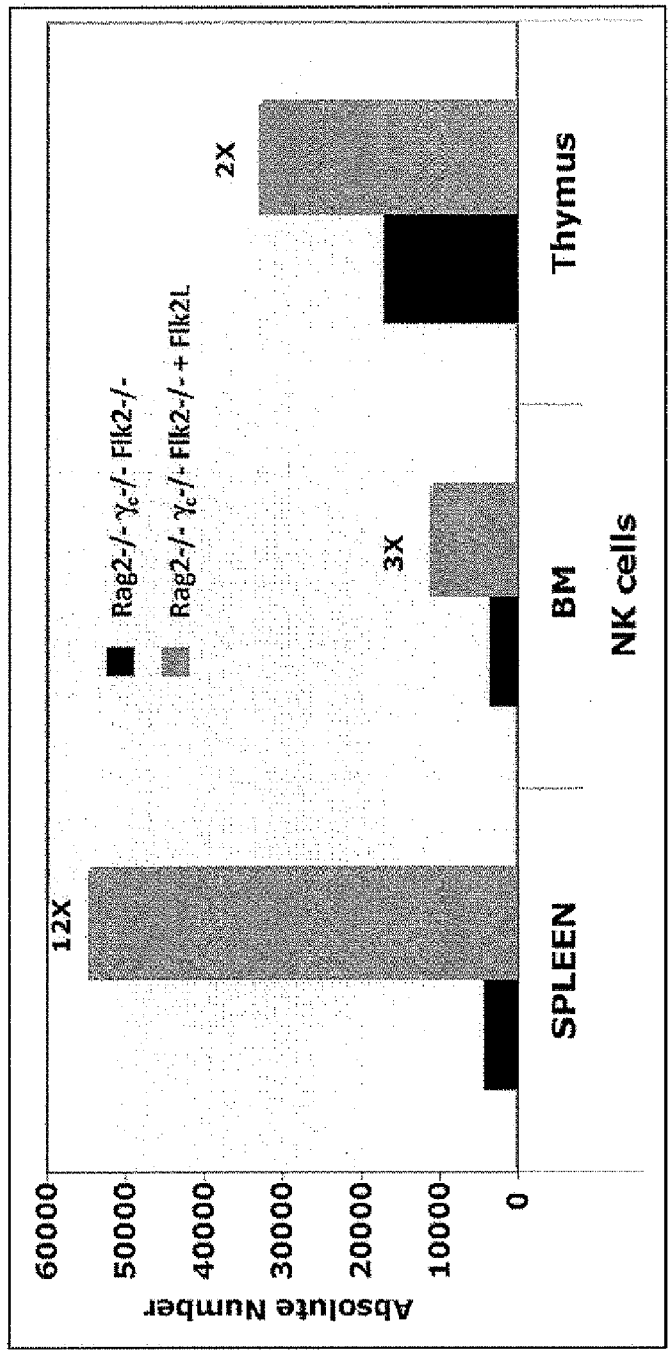

FIG. 5. Human NK cells are increased in "DC boosted" HIS mice. HIS mice were generated in the indicated recipients as described in FIG. 3. CD56$^+$CD3$^-$NK cells were enumerated in the spleen, thymus and bone marrow (BM).

5. DETAILED DESCRIPTION OF THE INVENTION

The present invention relates to Rag$^{-/-}$γc$^{-/-}$Flk2$^{-/-}$ mice that may be used as recipient hosts for human haematopoietic precursor transplantation, to generate new human/mouse chimeras that have unique features relating to the development and functional capacities of human DC subsets. The mice of the invention represent a completely humanized model, easy to develop, that can be used to study the development and regulation of the human immune system in vivo. The mice of the invention provide a model useful in the development and optimization of vaccines or immunotherapies with maximum efficacy in vivo for human use. Specifically, such mice enable a complete analysis of the components of the immune response to a human antigen (pathogen, tumor, auto-antigen) in a single animal, as well as an evaluation of the protection specifically conferred by vaccination against an antigenic challenge. It is also possible to study how these responses cooperate. Therefore, this model is useful to develop more efficient prophylactic or curative immunotherapies against human pathogens, cancer and auto-immune diseases. The mice of the invention represent an optimized tool for basic and applied immunology studies.

Definitions

"deficiency for" refers to the lack of a molecular or cellular function.

"mutation" refers to the substitution, insertion, deletion of one or more nucleotides in a polynucleotide sequence.

"deficient gene", "inactivated gene", "null allele" refers to a gene comprising a spontaneous or targeted mutation that results in an altered gene product lacking the molecular function of the wild-type gene.

"disrupted gene" refers to a gene that has been inactivated using homologous recombination or other approaches known in the art.

"xenogenic", "xenogenic species" refers to a non-mouse vertebrate.

γc$^{-/-}$ refers to a disruption of the IL-2 receptor γ chain

Flk2$^{-/-}$ refers to a disruption of the Flk2 gene (fetal liver kinase-2 gene)

Rag$^{-/-}$ refers to a disruption of the recombinant activating gene 1 (Rag 1) and/or recombinant activating gene 2 (Rag2).

5.1. Transgenic Animal Model System

The present invention relates to a transgenic animal model system based on the development of transgenic mice bearing components of the human immune system, including human DCs. The transgenic mice according to the present invention comprise three genes that are inactivated by a spontaneous mutation or a targeted mutation (deficient genes). These mutations which are well-known to those of ordinary skill in the art include, for example: a first mutation which is a disruption of the recombination activating gene Rag1 and/or Rag2 (Mombaerts et al., Cell, 1992, 68, 869-877; Takeda et al., Immunity, 1996, 5, 217-228), a second mutation which is a disruption of the IL-2 receptor γ chain (or common cytokine receptor γ chain (γ$_c$)) gene (IL-2Rγ$^{-/-}$ or γ$_c$$^{-/-}$; DiSanto et al., 1995, Proc Natl Acad Sci USA 92; 377-381), and a third mutation which is a disruption of the Flk2 gene (Mackarehtschian K et al., 1995 Immunity 3:147-61)

Mutant mice that are Rag2$^{-/-}$, γC$^{-/-}$, Rag2$^{-/-}$γC$^{-/-}$, and Flk2$^{-/-}$ and their preparation and characteristics are known. (See Shinkai Y et al., 1992, Cell 68:855; DiSanto J P et al., 1995, Proc Natl Acad Sci USA. 92:377-81; Andersson A et al., 1997, Eur J Immunol. 27:1762-8; and Mackarehtschian K et al., 1995 Immunity 3:147-61). In an embodiment of the invention, the mutations are placed in an appropriate genetic background. Such backgrounds are well-known to those of ordinary skill in the art and include, for example, a Balb/c background. In a specific embodiment of the invention, the mouse according to the present invention comprises the genotype Rag2$^{-/-}$/γc$^{-/-}$/Flk2$^{-/-}$.

Methods for generating transgenic animals with targeted mutations and/or transgene expression via embryo manipulation and microinjection, particularly animals such as mice, have become conventional in the art and are described, for example, in U.S. Pat. No. 4,736,866 by Leder et al. and U.S. Pat. No. 4,870,009 Evans et al., U.S. Pat. No. 4,873,191 by Wagner et al., and in Hogan, B., Manipulating the Mouse Embryo, (Cold Spring Harbor Laboratory Press, Cold Spring Harbor, N.Y. 1986), incorporated herein by reference in their entirety.

The mouse of the present invention may be produced by successive crossing of mice carrying one or more mutation(s)/transgene(s) of interest as defined above, and screening of the progenies until double and triple mutants and double and triple transgenics are obtained. Methods for performing such successive crossings of mice are well known to those of skill in the art.

The transgenic mice of the invention, carrying one or more of the desired mutations/transgenes of interest may be generated using homologous recombination which is a general approach for targeting mutations to a preselected, desired gene sequence of a cell in order to produce a transgenic animal (Mansour et al., Nature, 1988, 336:348-352; Capecchi, M. R., Trends Genet., 1989, 5:70-76. Capecchi, M. R. Science, 1989, 244:1288-1292; Capecchi et al., In: *Current Communications in Molecular Biology*: Capecchi, M. R. (Ed.), (Cold Spring Harbor Press, Cold Spring Harbor, N.Y. (1989), pp. 45-52; Frohman et al., Cell, 1989, 56:145-147). Gene targeting involves the use of standard recombinant DNA techniques to introduce a desired mutation into a cloned DNA sequence of a chosen locus. In order to utilize the "gene targeting" method, the gene of interest must have been previously cloned, and the intron-exon boundaries determined. The method results in the insertion of a marker gene (e.g., an nptII gene) into a translated region of a particular gene of interest. Thus, use of the gene targeting method results in the gross destruction of the gene of interest. Significantly, the use of gene targeting to alter a gene of a cell results in the formation of a gross alteration in the sequence of that gene. The mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Chimeric or transgenic animal cells may be prepared by introducing one or more DNA molecules into a cell, which may be a precursor pluripotent cell, such as an ES cell, or equivalent (Robertson, E. J. In: *Current Communications in Molecular Biology*, Capecchi, M. R. (ed.), Cold Spring Harbor Press, Cold Spring Harbor, N.Y. (1989), pp. 39-44). The term "precursor" is intended to denote only that the pluripotent cell is a precursor to the desired ("transfected") pluripotent cell, which is prepared in accordance with the teachings of the present invention. The pluripotent (precursor or transfected) cell can be cultured in vivo in a manner known in the art (Evans et al., Nature, 1981, 292:154-156), to form a chimeric or transgenic animal. Any ES cell can be used in accordance with the present invention. It is, however, preferred to use primary isolates of ES cells. Such isolates can be obtained directly from embryos, such as the CCE cell line disclosed by Robertson, E. J. (In: *Current Communications in Molecular Biology*, Capecchi, M. R. (ed.), Cold Spring Harbor Press, Cold Spring Harbor, N.Y. (1989). pp. 39-44), or from the clonal isolation of ES cells from the CCE cell line (Schwartzberg et al., Science, 1989, 246:799-803, which reference is incorporated herein by reference). Such clonal isolation can be accomplished according to the method of E. J. Robertson (In: *Teratocarcirnomas and Embryonic Stem Cells: A Practical Approach*, (E. J. Robertson, Ed.), IRL Press, Oxford, 1987), which reference and method are incorporated herein by reference. The purpose of such clonal propagation is to obtain ES cells, which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage. An example of ES cell lines which have been clonally derived from embryos, are the ES cell lines, ABI (hprt$^+$) or AB2.1 (hprt$^+$). The ES cells are preferably cultured on stromal cells (such as STO cells (especially SNC4 STO cells) and/or primary embryonic fibroblast cells) as described by E. J. Robertson (In: *Teratocarcinomas and Embryonic Stem Cells: A Practical Approach*, (E. J. Robertson, Ed. IRL Press, Oxford 1987, pp 71-112), which reference is incorporated herein by reference. Methods for the production and analysis of chimeric mice are disclosed by Bradley, A. (In: *Teratocarcinomas and Embryonic Stem Cells: A Practical Approach*, (E. J. Robertson, Ed), IRL Press, Oxford, 1987, pp 113-151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("LIF") (Gough et al., Reprod. Fertil. Dev., 1989, 1:281-288; Yamamori et al., Science, 1989, 246:1412-1416). Since the gene encoding LIF has been cloned (Gough et al., Reprod. Fertil. Dev., 1989, 1:281-288), it is especially preferred to transform stromal cells with this gene, by means known in the art, and to then culture the ES cells on transformed stromal cells that secrete LIF into the culture medium.

The invention relates also to an isolated cell from a transgenic mouse as defined above. Preferably, said cell has the genotype Rag$^{-/-}$, γc$^{-/-}$, Flk2$^{-/-}$.

In an embodiment of the invention, the transgenic mouse as defined above, Rag$^{-/-}$, γ$_c$$^{-/-}$, Flk2$^{-/-}$, is used as a recipient host for the transplantation of xenogenic hematopoietic precursors, for example human hematopoietic precursors (also referred to herein as stem cells or progenitor cells). Accordingly, the transgenic mice of the invention, which are deficient for Flk2, Rag1 and/or Rag2 and c are further engrafted with human hematopoietic stem cells (HSCs). Such HSCs may be derived from, for example, fetal liver, cord blood or adult bone marrow and are characterized by expression of CD34. The cells may be cultured for an appropriate time before transplantation, to improve the engraftment rate of the hematopoietic progenitors into the transgenic mouse. The number of cells that are transplanted is determined so as to obtain optimal engraftment into the transgenic mouse. For example, human CD34$^+$ cells (from 10$^4$ to 10$^6$ cells), isolated from cord blood or fetal liver are transplanted intraperitoneally, intra-hepatically, or intravenously, for example via a facial vein, into sub-lethally irradiated newborn transgenic mice. The engraftment of cells into immunodeficient mice can be accomplished using methods well known to those of skill in the art (Traggiai et al., Science, 2004, 304, 104-107; Ishikawa et al., Blood, 2005, 106, 1565-1573; Gimeno et al., Blood, 2004, 104, 3886-3893; Vodyanik et al., Blood, 2005, 105, 617-626).

In addition, the hematopoietic progenitor cells may be genetically modified prior to transplantation. They may advantageously comprise a genetic modification that improves the differentiation of hematopoietic precursors into functional T, B and dendritic cells. These modifications are well-known to those skilled in the art. For example, conditional expression of STAT5 in the hematopoietic precursor cells may be obtained as described in Kyba and Daley (Experimental Hematology, 2003, 31, 994-1006).

The present invention further provides a method for compromising mouse DC development and thereby selectively increasing human DC development in the HIS mice of the invention. Mouse DC development is compromised in Balb/c Rag2$^{-/-}$γc$^{-/-}$ Flk2$^{-/-}$ recipient mice as a result of the inability to respond to Flk2L. The method of the invention is based on the observation that treatment of xenografted Balb/c Rag2$^{-/-}$γc$^{-/-}$Flk2$^{-/-}$ mice with recombinant Flk2L (also referred to as Flt3 Ligand) in vivo significantly enhanced the frequency and absolute numbers of mature human DC (both plasmacytoid and conventional) without any effect on endogenous mouse DC. Moreover, human granulocytes, monocytes, as well as human NK cells and T cells, were increased in HIS mice receiving Flk2L. Accordingly, in a specific embodiment of the invention, the numbers of DCs in said engrafted transgenic mice can be induced through administration of Flk2L and/or Flk2 agonists. Such Flk2L agonist include any molecule capable of increasing quantities of human DCs, including but not limited to small protein molecules or agonist antibodies that mimic the activity of Flk2L. In a non-limiting embodiment of the invention, murine Flk2L or human Flk2L may be administered to the mice of the invention to increase the numbers of human DCs. Alternatively, Flk2L may be provided through subcutaneous implantation of cells that naturally express Flk2L or cells that have been transfected with a cDNA encoding Flk2L. Such cells include, for example, the B16 melanoma cell line which expresses Flk2L. Still further, recombinant Flk2L protein, including but not limited to a human fusion Flk2L-Ig protein (available from BioXCell) may be administered (e.g. intravenously or intraperitoneally) to stimulate the production of human DCs.

5.2. Screening Assays

The transgenic animals of the invention provide a novel means to monitor human immune responses, test vaccine candidates, screen potential immune adjuvants and understand subversion mechanisms that operate by directly modifying human DC function and/or indirectly modifying human T cells or NK cells.

Mice bearing components of the human immune system (HIS) are considered an important preclinical model for advancing the understanding of human immune responses and represent an important intermediate for testing human vaccine candidates and for developing novel therapeutics. DC are a heterogeneous subset of hematopoietic cells that act as critical sensors of pathogens, 'stress' and inflammation. DC are an integral component of immune system and control immune responses at several levels. Specifically, (i) DC sustain and amplify innate immune components that represent a first line defense against infection and cancer and (ii) DC initiate and specify adaptive immune responses (both cellular and humoral) that eliminate foreign pathogens or tumors and provide long-lasting memory responses. As described herein, small numbers of DC resembling mature human DC are detectable in lymphoid tissues of Balb/c Rag2$^{-/-}\gamma$c$^{-/-}$ HIS mice following transfer of human hematopoietic stem cells, but their frequency is low and their development is variable. In contrast, existing immunodeficient recipients used to generate HIS mice have a normal endogenous mouse DC compartment. As a result, the immune responses observed in current HIS mouse models are primarily controlled by DCs of mouse origin. Since human and mouse DCs respond differently during immune responses, a HIS mouse model with a minimal mouse DC compartment and a maximal human DC compartment would more closely mimic normal human immune responses.

Accordingly, the invention relates to a method for analysing the development and function of the immune system of a xenogenic species in vivo, for example the human immune system in vivo. The method of the invention comprises:

(i) engrafting xenogenic hematopoietic progenitor cells, for example human hematopoietic progenitor cells, into a Rag$^{-/-}$, $\gamma_c^{-/-}$, Flk2$^{-/-}$ transgenic mouse; and (ii) assaying for the presence of functional T, B or dendritic cells of the xenogenic species, for example human, in the transplanted mouse.

In a specific embodiment of the invention, the xenogenic hematopoietic cells are human cells. In yet another embodiment of the invention, the engrafted cells are cells that have been genetically modified prior to engraftment.

In a particular embodiment of the invention, the method for analysing the development and function of the immune system of a xenogenic species in vivo, further comprises the administration of Flk2L to the transgenic mouse.

The presence of functional human T-, B- and dendritic (DC)-cells is assayed by any technique well-known in the art. For example, several weeks after transplantation of the hematopoietic progenitor cells (from 4 weeks to about 12 weeks), bone marrow, spleen, thymus and peripheral blood may be analysed by flow cytometry and/or immunohistochemistry, based on expression of appropriate markers. The level of engraftment is determined by measuring the human leukocytes (CD45$^+$) cell number and the proportion of T cells (CD45$^+$, CD3$^+$), B cells (CD45$^+$, CD19$^+$) and dendritic cells (CD45$^+$, CD11$^+$ and CD45$^+$, CD11$^-$CD123$^+$) in the different lymphoid organs.

The presence of functional human T cells may be assayed measuring the proliferative capacity of T cells, for example to an alloantigen (Mixed Lymphocyte reaction) or their capacity to produce cytokines (ELISPOT, intracellular flow cytometry). The diversity of the T cell repertoire may be assayed by immunoscope analyses.

The presence of functional human B cells may be assayed by measuring, either the total human immunoglobulins in mice sera, the hIgG and the IgM by ELISA or the immunoglobulin secreting cells, by ELISPOT.

The presence of functional DC may be assayed in vivo or ex vivo by measuring their capacity to induce the proliferation of allogenic T cells (CD11$^-$ cells) or their capacity to produce IFN-$\alpha$ after stimulation (CD11$^+$ cells).

The invention relates also to a method for analysing the immune response of a xenogenic species to an antigen in vivo, for example the human immune response to an antigen in vivo. The method of the invention comprises:

(i) contacting a Rag$^{-/-}$, $\gamma_c^{-/-}$, Flk2$^{-/-}$ transgenic mouse of the invention with an antigen of interest, and, (ii) assaying for the presence of an immune response.

In such assays, the immune response observed in the presence of an antigen may be compared to the immune response observed in the absence of an antigen, or in the presence of a different antigen or antigen preparation, to assess and/or compare the activity of the tested antigen.

Assaying for the presence of an immune response, includes but is not limited to detection of an increase, decrease or changes in the properties of the immune response.

In an embodiment of the invention, the transgenic mouse is a Rag$^{-/-}$, $\gamma_c^{-/-}$, Flk2$^{-/-}$ mouse into which xenogenic hematopoietic progenitor cells have been engrafted.

In a specific embodiment of the invention, the xenogenic hematopoietic progenitor cells are human cells. In yet another embodiment of the invention, the engrafted cells are cells that have been genetically modified prior to engraftment.

In a particular embodiment of the invention, the method for analysing the immune response of a xenogenic species to an antigen in vivo, further comprises the administration of Flk2L to the transgenic mouse.

The presence of an immune response may be detected by assaying for a humoral response, a T-helper cell response, a T-cytotoxic cell response, a NK cell-mediated cytotoxic cell response, NK cell-mediated production of cytokines and/or chemokines, a DC-mediated cytotoxic response, a DC-mediated production of cytokines and/or chemokines, or an innate lymphocyte inflammatory response in the mouse.

The antigen is preferably injected after a time sufficient to allow the reconstitution of a functional immune system. Alternatively, the antigen may be injected prior to reconstitution of a functional immune system to assess the effect of antigen on immune development.

The antigen may be natural, recombinant or synthetic. The antigen can comprise a polypeptide sequence or a polynucleotide sequence, which can comprise RNA, DNA, or both. In one embodiment, the antigen comprises at least one polynucleotide sequence operationally encoding one or more antigenic polypeptides. Used in this context, the word "comprises" intends that at least one antigenic polypeptide is provided by the transcription and/or translation apparatus of a host cell acting upon an exogenous polynucleotide that encodes at least one antigenic polypeptide. Antigens of the invention can be any antigenic molecule. Antigenic molecules include: proteins, lipoproteins, and glycoproteins, including viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, and tumor associated antigens such as carcinoembryonic antigen (CEA), CA 15-3, CA 125, CA 19-9, prostate specific antigen (PSA); carbohydrates, including naturally-occurring and synthetic polysaccharides and other polymers such as ficoll, dextran, carboxymethyl cellulose, agarose, polyacrylamide and other acrylic resins, poly (lactide-co-glycolide), polyvinyl alcohol, partially hydrolyzed polyvinyl acetate, polyvinylpyrrolidine, Group B Streptococcal and Pneumococcal capsular polysaccharides (including type III). *Pseudomonas aeruginosa* mucoexopolysaccharide, and capsular polysaccharides (including fisher type I), and *Haemophilus influenzae* polysaccharides (including PRP); haptens, and other moieties comprising low molecular weight molecules, such as TNP, saccharides, oligosaccharides, polysaccharides, peptides, toxins, drugs, chemicals, and allergens; and haptens and antigens derived from bacteria, fungi, viruses, parasites and prions. Bacteria include for example: *C. diphtheriae, B. pertussis, C. tetani, H. influenzae, S. pneumoniae, E. Coli*, Klebsiella, *S. aureus, S. epidermidis, N. meningiditis, B. anthracis*, Listeria, *Chlamydia trachomatis* and *pneumoniae*, Rickettsiae, Group A Streptococcus, Group B Streptococcus, *Pseudomonas aeruginosa*, Salmonella, Shigella, Mycobacteria (*Mycobacterium tuberculosis*) and Mycoplasma. Viruses include for example: Polio, Mumps, Measles, Rubella, Rabies, Ebola, Hepatitis A, B, C, D and E, Varicella Zoster, Herpes simplex types 1 and 2, Parainfluenzae, types 1, 2 and 3 viruses, Human Immunodeficiency Virus I and II, RSV, CMV, EBV, Rhinovirus, Influenzae virus A and B, Adenovirus, Coronavirus, Rotavirus and Enterovirus. Fungi include for example: *Candida* sp. (*Candida albicans*). Parasites include for example: Plasmodium (*Plasmodium falciparum*), *Pneumocystis carinii*, Leishmania, and Toxoplasma.

The presence of an immune response to the antigen is assayed by any technique well-known in the art. For example, the presence of a humoral response to the antigen is assayed by measuring, either the titer of antigen-specific antibodies in mice sera, by ELISA, or the number of antibody secreting cells, by ELISPOT. The presence of a T-helper cell response to the antigen is assayed by a T cell proliferation assay or cytokine production assays (ELISPOT or intracellular flow cytometry). The presence of a T-cytotoxic cell response to the antigen is assayed by a CTL assay in vitro or in vivo (Barber D L et al., J Immunol, 2003, 171:27-31).

The method of the invention may also be used for mapping antigens, for screening new antigens, as well as for evaluating the immunogenicity of different antigen preparations for use as human vaccine.

The invention further relates to a method for analysing the capacity of the immune response of a xenogenic species to be modified by an adjuvant in vivo, for example modification of the human immune response by an adjuvant in vivo. The method of the invention comprises the steps of:

(i) contacting a $Rag^{-/-}$, $\gamma_c^{-/-}$, $Flk2^{-/-}$ transgenic mouse with an antigen of interest in the presence of an adjuvant to be tested; and (ii) assaying for the presence of an immune response.

In such assays, the immune response observed in the presence of an adjuvant may be compared to the immune response observed in the absence of an adjuvant, or in the presence of a different adjuvant, to assess and/or compare the activity of the tested adjuvant.

Assaying for the presence of an immune response, includes but is not limited to detection of an increase, decrease or changes in the properties of the immune response.

In an embodiment of the invention, the transgenic mouse is a $Rag^{-/-}$, $\gamma_c^{-/-}$, $Flk2^{-/-}$ mouse into which xenogenic hematopoietic progenitor cells have been engrafted.

In a specific embodiment of the invention, the xenogenic hematopoietic progenitor cells are human cells. In yet another embodiment of the invention, the engrafted cells are cells that have been genetically modified prior to engraftment.

In a particular embodiment of the invention, the method for analysing the capacity of the immune response of a xenogenic species to be modified by an adjuvant in vivo further comprises the administration of Flk2L to the transgenic mouse.

The presence of an immune response may be detected by assaying for a humoral response, a T-helper cell response, a T-cytotoxic cell response, a NK cell-mediated cytotoxic cell response, NK cell-mediated production of cytokines and/or chemokines, a DC-mediated cytotoxic response, a DC-mediated production of cytokines and/or chemokines, or an innate lymphocyte inflammatory response in the mouse.

The antigen in the presence of an adjuvant to be tested is preferably injected after a time sufficient to allow the reconstitution of a functional immune system. The adjuvant may be injected prior to, combined with or after the antigen. Alternatively, the effect of adjuvant on immune development may be assessed by injection prior to reconstitution of a functional immune system.

The adjuvant may be natural, recombinant or synthetic. The adjuvant can comprise a polypeptide sequence or a polynucleotide sequence, which can comprise RNA, DNA, or both. In one embodiment, the adjuvant comprises at least one polynucleotide sequence operationally encoding one or more adjuvants. Used in this context, the word "comprises" intends that at least one adjuvant is provided by the transcription and/or translation apparatus of a host cell acting upon an exogenous polynucleotide that encodes at least one adjuvant. Adjuvants of the invention can be any molecule with adjuvant activity. Adjuvants include: proteins, lipoproteins, and glycoproteins, including viral, bacterial, parasitic, animal, and fungal proteins such as toxoids, bacterial outer membrane proteins (including meningococcal outer membrane protein), carbohydrates, including naturally-occurring and synthetic polysaccharides and other polymers such as ficoll, dextran, carboxymethyl cellulose, agarose, polyacrylamide and other acrylic resins, poly (lactide-co-glycolide), polyvinyl alcohol, partially hydrolyzed polyvinyl acetate, polyvinylpyrrolidine, Group B Streptococcal and Pneumococcal capsular polysaccharides (including type III), *Pseudomonas aeruginosa* mucoexopolysaccharide, and capsular polysaccharides (including fisher type I), and *Haemophilus influenzae* polysaccharides (including PRP); haptens, and other moieties comprising low molecular weight molecules, such as saccharides, oligosaccharides, polysaccharides, peptides, toxins, drugs, chemicals, and allergens; and haptens and antigens derived from bacteria, fungi, viruses, parasites and prions. Bacteria that contain adjuvant compounds include for example: *C. diphtheriae, B. pertussis, C.*

*tetani, H. influenza. S. pneumoniae. E. Coli*, Klebsiella, *S. aureus. S. epidermidis. N. meningiditis, B. anthracis*, Listeria, *Chlamydia trachomatis* and *pneumoniae*, Rickettsiae, Group A Streptococcus, Group B Streptococcus, *Pseudomonas aeruginosa*, Salmonella, Shigella, Mycobacteria (*Mycobacterium tuberculosis*) and Mycoplasma. Viruses providing potential adjuvant activity include for example: Polio, Mumps, Measles, Rubella. Rabies, Ebola, Hepatitis A, B, C, D and E, Varicella Zoster, Herpes simplex types 1 and 2, Parainfluenzae, types 1, 2 and 3 viruses, Human Immunodeficiency Virus I and II, RSV, CMV, EBV, Rhinovirus, Influenzae virus A and B, Adenovirus, Coronavirus, Rotavirus and Enterovirus. Fungi include for example: *Candida* sp. (*Candida albicans*). Parasites include for example: Plasmodium (*Plasmodium falciparum*), *Pneumocystis carinii*, Leishmania, and Toxoplasma.

The presence of a modified immune response to the antigen in the presence of an adjuvant is assayed by any technique well-known in the art.

The presence of a humoral response to the antigen is assayed by measuring, either the titer of antigen-specific antibodies in mice sera, by ELISA, or the number of antibody secreting cells, by ELISPOT.

The presence of a T-helper cell response to the antigen is assayed by a T cell proliferation assay or cytokine production assays (ELISPOT or intracellular flow cytometry).

The presence of a T-cytotoxic cell response to the antigen is assayed by a CTL assay in vitro or in vivo (Barber D L et al., J Immunol, 2003, 171:27-31).

The method of the invention may be used for classifying adjuvants, for screening new adjuvants, as well as for evaluating the potential effects of adjuvants in human vaccine candidates.

The present invention provides for compositions comprising an effective amount of an antigen identified using the screening methods of the invention which is capable of effectively stimulating an immune response, and a pharmaceutically acceptable carrier. The present invention also provides for compositions comprising an effective amount of an adjuvant identified using the screening methods of the invention which is capable of effectively stimulating an immune response, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In yet another embodiment of the invention, the transgenic animals of the invention provide a model system to screen for, or identify, compounds that modulate (inhibit or activate) the development, homeostasis, maturation or function of human DCs. Accordingly, the present invention provides for methods for identifying a compound that induces DC development, homeostasis, maturation or function, comprising (i) contacting a $Rag^{-/-}$, $\gamma c^{-/-}$, $Flk2^{-/-}$ transgenic mouse of the invention with a test compound and (ii) measuring the level of DC development, homeostasis, maturation or function; wherein an increased in the level of DC development, homeostasis, maturation or function, in the presence of the test compound indicates that the test compound induces DC: development, homeostasis, maturation or function.

The present invention also provides for methods for identifying a compound that inhibits DC development, homeostasis, maturation or function, comprising (i) contacting a $Rag^{-/-}$, $\gamma c^{-/-}$, $Flk2^{-/-}$ transgenic mouse of the invention with a test compound and measuring the level of DC development, homeostasis, maturation or function; (ii) in a separate experiment, measuring the level of DC development, homeostasis, maturation or function, in the absence of the test compound, where the conditions are essentially the same as in part (i) and then (iii) comparing the level of DC development, homeostasis, maturation or function measured in part (i) with the level of DC development, homeostasis, maturation or function in part (ii), wherein a decrease level of DC development, homeostasis, maturation or function in (i) compared to (ii) indicates that the test compound is an inhibitor of DC development, homeostasis, maturation or function.

In an embodiment of the invention, the transgenic mouse, for use in screening for, or identification of, compounds that modulate (inhibit or activate) the development, homeostasis, maturation or function of human DCs, is a $Rag^{-/-}$, $\gamma_c^{-/-}$, $Flk2^{-/-}$ mouse into which xenogenic hematopoietic progenitor cells have been engrafted.

In a specific embodiment of the invention, the xenogenic hematopoietic progenitor cells are human cells. In yet another embodiment of the invention, the engrafted cells are cells that have been genetically modified prior to engraftment.

In a particular embodiment of the invention, the methods for use in screening for, or identification of, compounds that modulate (inhibit or activate) the development, homeostasis, maturation or function of human DCs, further comprises the administration of Flk2L to the transgenic mouse.

The animal model system of the invention, bearing components of the human immune system including expression of human DCs, further provides a means for assaying the efficacy, toxicity, or side effects of newly developed therapies including immunotherapies. Newly developed cancer treatments may also be tested for their efficacy, toxicity, and/or presence of side effects.

Infectious disease treatments may be assayed using the transgenic mice of the invention. Such infectious diseases include, for example, bacterial, viral, fungal or parasitic diseases. In addition, treatments designed to inhibit transplant rejection may be assayed using the transgenic mice of the invention.

The transgenic animals of the invention also provide an animal model system for screening for compounds that modulate the activity, or level of expression, of Flk2L and/or Flk2, thereby regulating the development, homeostasis, maturation or function of DCs. Such compounds may be used in immunotherapies for treatment of pathogenic diseases, cancer, autoimmune and inflammatory diseases and for treatment of transplant patients.

The present invention provides for methods for identifying a compound that increases Flk2L expression or activity, i.e., an agonist, thereby inducing DC development, homeostasis, maturation or function, comprising (i) contacting a $Rag^{-/-}$, $\gamma c^{-/-}$, $Flk2^{-/-}$ transgenic mouse of the invention with a test compound and (ii) measuring the level of DC development, homeostasis, maturation or function; wherein an increased in the level of DC development, homeostasis, maturation or function in the presence of the test compound indicates that the test compound increases Flk2L expression or activity.

The present invention also provides for methods for identifying a compound that inhibits Flk2 or Flk2L activity or expression, i.e., an antagonist, thereby inhibiting DC development, homeostasis, maturation or function comprising (i) contacting a $Rag^{-/-}$, $\gamma c^{-/-}$, $Flk2^{-/-}$ transgenic mouse of the invention with a test compound, in the presence of Flk2L and measuring the level of DC development, homeostasis, maturation or function: (ii) in a separate experiment, contacting a transgenic mouse of the invention with Flk2L and measuring the level of DC development, homeostasis, maturation or function, where the conditions are essentially the same as in part (i) and then (iii) comparing the level of DC development, homeostasis, maturation or function measured in part (i) with the level of DC development, homeostasis, maturation or function in part (ii), wherein a decrease level of DC development, homeostasis, maturation or function in (i) compared to (ii) indicates that the test compound is a Flk2 or Flk2L inhibitor.

In an embodiment of the invention, the transgenic mouse, for use in screening for compounds that modulate the activity, or level of expression, of Flk2L and/or Flk2, thereby regulating the development, homeostasis, maturation or function of DCs, is a $Rag^{-/-}$, $\gamma c^{-/-}$, $Flk2^{-/-}$ mouse into which xenogenic hematopoietic progenitor cells have been engrafted.

In a specific embodiment of the invention, the xenogenic hematopoietic cells are human cells. In yet another embodiment of the invention, the engrafted cells are cells that have been genetically modified prior to engraftment.

The ability of a test molecule to modulate DC development, homeostasis, maturation or function may be measured using standard biochemical and physiological techniques. In a specific embodiment of the invention, DC development, homeostasis, maturation or function can be measured through detection of specific cell surface markers that are expressed on the surface of DCs as they mature and differentiate. For example, as DCs differentiate the level of cell surface CD80, CD86 and MHC class I and II expression increases. DC differentiation can also be measured by DC effector functions including chemokine and cytokine production.

Preferred methods for the identification of such cell surface markers in the biological sample of a test animal can involve, for example, immunoassays wherein cell surface markers are detected by their interaction with a cell surface specific antibody. Such antibodies include, but are not limited to anti-CD80, anti-CD86 and anti-MHC class I and class II antibodies, to name a few. Antibodies useful in the present invention can be used to quantitatively or qualitatively detect the presence of DC surface markers. In addition, reagents other than antibodies, such as, for example, polypeptides that bind specifically to the cell surface marker proteins can be used in assays to detect the level of protein expression. Immunoassays useful in the practice of the invention include but are not limited to assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

A sample of a biological fluid or biological tissue to be assessed for levels of dendritic cells, such as blood or other biological tissue, is obtained from the test animal. Immunoassays for detecting DCs typically comprise contacting the biological sample, such as a blood or tissue sample derived from the test animal, with an anti-cell surface marker antibody under conditions such that an immunospecific antigen-antibody binding reaction can occur, and detecting or measuring the amount of any immunospecific binding by the antibody. In a specific aspect, such binding of antibody, for example, can be used to detect the presence of one or more cell surface marker proteins specifically expressed on differentiated DCs wherein the detection of said proteins is an indication of DC differentiation.

Detection of antibodies bound to DC surface specific markers may be accomplished using a variety of methods. For example, by radioactively labeling the antibodies or antibody fragments, it is possible to detect cytidine deaminase protein expression through the use of a radioimmunoassay (RIA) (see, for example, Weintraub, B., Principles of Radioimmunoassays, Seventh Training Course on Radioligand Assay Techniques, The Endocrine Society, March 1986). The radioactive isotope can be detected by such means as the use of a gamma counter or a scintillation counter or by autoradiography. The antibody may also be labeled with a fluorescent compound. Among the most commonly used fluorescent labeling compounds are fluorescein isothiocyanate, rhodamine, phycoerythrin and fluorescamine. Likewise, a bioluminescent compound may be used to label the antibody. The presence of a bioluminescence protein is determined by detecting the presence of luminescence. Important bioluminescence compounds for purposes of labeling are luciferin, luciferase and aequorin.

The assays described above can identify compounds which modulate the maturation or activity of CDs. For example, compounds that affect Flk2 or Flk2L activity include but are not limited to compounds that bind to Flk2 or Flk2L, and either activate the ligand/receptor activity (agonists) or block the ligand/receptor activity (antagonists). Alternatively, compounds (agonists or antagonists) may be identified that do not bind directly to Flk2 or Flk2L but which are capable of altering their activity by altering the activity of a protein involved in the Flk2 mediated signal transduction pathway.

The compounds which may be screened in accordance with the invention include, but are not limited to, small organic or inorganic compounds, peptides, antibodies and fragments thereof, and other organic compounds e.g., peptidomimetics). Compounds may include, but are not limited to, peptides such as, for example, soluble peptides, including but not limited to members of random peptide libraries (see, e.g., Lam, K. S. et al., 1991, Nature 354:82-84; Houghten, R. et al., 1991, Nature 354:84-86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and Fab, F(ab')2 and Fab expression library fragments, and epitope binding fragments thereof), and small organic or inorganic molecules.

The present invention provides for compositions comprising an effective amount of a compound identified using the screening methods of the invention which are capable of modulating (increasing or decreasing) the number of mature DCs, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The present invention relates to methods and compositions for preventing the occurrence or progression of infectious diseases, including but not limited to those arising from infections with pathogens such as viruses, bacteria, fungi or parasites. The method comprises administering to a mammal a compound that induces DC development, homeostasis, maturation or function in an amount effective to prevent the occurrence of the infectious disease, or to slow or halt the progression of said disease. The compounds can be administered as a therapeutic to treat an existing condition or as a prophylactic in advance of exposure to pathogen.

The present invention relates to methods and compositions for preventing the occurrence or progression of a cancer or pre-cancerous condition. The method comprises administering to a mammal a compound that induces DC development, homeostasis, maturation or function in an amount effective to prevent the occurrence of the cancer, or to slow or halt the progression of said disease. The compounds can be administered as a therapeutic to treat an existing condition or as a prophylactic in advance of exposure to a carcinogenic compound or event.

The present invention also relates to methods and compositions for preventing transplant rejection in transplant patients. The method comprises administering to a mammal a compound that induces DC development, homeostasis, maturation or function in an amount effective to prevent transplant rejection.

The present invention relates to methods and compositions for preventing the occurrence or progression of an autoimmune disorder. The method comprises administering to a mammal a compound that inhibits DC development, homeostasis, maturation or function in an amount effective to prevent the occurrence of the autoimmune disorder, or to slow or halt the progression of said disease.

The present invention also relates to methods and compositions for preventing the occurrence or progression of an inflammatory disorder. The method comprises administering to a mammal a compound that inhibits DC maturation in an amount effective to prevent the occurrence of the autoimmune disorder, or to slow or halt the progression of said disease. Such anti-inflammatory conditions include, but are not limited to arthritis, asthma and allergies.

Various delivery systems are known and can be used to administer a compound capable of modulating DC development, homeostasis, maturation or function, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses maybe extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. Ausebel, 2000, Wiley and son Inc. Library of Congress, USA); Molecular Cloning: A Laboratory Manual, Third Edition, (Sambrook et al, 2001, Cold Spring Harbor, N.Y.: Cold Spring Harbor Laboratory Press); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In Enzymology (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

6. EXAMPLE 1

6.1 Materials and Methods

Generation of Recipient Mouse Strains and HIS Mice

Rag2$^{-/-}$γc$^{-/-}$ mice (Colucci et al., 1999, Journal of Immunology 162:2761-2765) and Flk2$^{-/-}$ mice (Mackarehtschian et al., 1995, Immunity 3:147-61) were backcrossed onto the Balb/c background and intercrossed to generate Rag2$^{-/-}$γc$^{-/-}$Flk2$^{-/-}$ recipients. All mice were maintained in isolators with autoclaved food and water. Mice with a human immune system (HIS) were generated as previously described (Gimeno et al., 2004, Blood 104:3886-3893; Huntington et al., 2009, Journal of Experimental Medicine 206:25-34). Briefly, newborn (3-5 day old) recipient mice received sub-lethal (3.3 Gy) total body irradiation from a Cs source, and were injected intra-hepatic (i.h.) with 1×10$^5$ sorted CD34$^+$CD38$^{-\ or}$ 5×10$^5$ CD34$^+$ human hematopoietic progenitor cells. All manipulations of HIS mice were performed under laminar flow.

Cell Preparation

Human fetal material was obtained from elective abortions, with gestational age ranging from 14 to 20 weeks. The use of this tissue was approved by the Medical Ethical Committees and was contingent on informed consent. Single cell suspensions of human fetal organs were achieved by mechanical disruption using a Stomacher® Biomaster lab system (Seward, Hadleigh, UK). Magnetic enrichment of CD34$^+$ cells (>98% pure) was performed by using the CD34 Progenitor Cell Isolation Kit (Miltenyi Biotech, Auburn, Calif.), after preparation of single-cell suspension and isolation of mononuclear cells by density gradient centrifugation over Ficoll-Hypaque (Nycomed Pharma, Roskilde, Denmark). Cell suspensions were prepared in RPMI medium with 2% fetal calf serum. Single cell suspensions were prepared as previously described (Huntington et al., 2009, Journal of Experimental Medicine 206:25-34).

Flk2L Treatment In Vivo

HIS mice were injected intraperitoneally with either recombinant human Flk2L (5 µg; Amgen; 3 times per week for 2 weeks), human Flk2L-Ig (10 µg: BioXcell; 3 times per week for 2 weeks) or mouse B16 melanoma cell lines (10$^6$ cells, s.c.) beginning at 8 weeks after reconstitution with CD34$^+$ human hematopoietic progenitor cells.

Phenotypic Analysis

Cell suspensions were labeled with mAb against the following human cell-surface markers: CD3 (SK7), CD4 (SK3), CD34 (581), CD8 (SK1), CD19 (HIB19), CD10 (H110a), CD38 (HB7), NKG2D (1D11), NKp46 (9E2), CD16 (3G8), CD161 (DX12), CD56 (B159), HLA-DR (L243), HLA-A/B/C (G46-2.6), CD117 (YB5.B8), IgD (IA6-2), IgM (G20-127), CD14 (M5E2), CD122 (Mik-β3), TCR-α/β (T10B9.1A-31), CD127 (hIL-7R-M21), CD11c (B-ly6), CD7 (M-T701), CD107a (1D4B), CD45 (2D1), CD69 (L78), Bcl-2 (Bcl-2/100), IFN-µ (XMG1.2) from BD Bioscience (San Jose, Calif.) and CD11b (ICRF44), CD25 (BC96), CD116 (4H1), CD83 (HB15e), anti-mouse NK1.1, CD11b, CD11c, F480 and DX5 from eBioscience (San Diego, Calif.). All washings and reagent dilutions were done with PBS containing 2% fetal calf serum (FCS). All acquisitions were performed using LSRII, Canto 1 or Canto 2 cytometers, cell sorting was performed using FACS ARIA; all machines were interfaced to the FACS-Diva software (BD Bioscience).

Analysis of Human Cytokines In Vitro

Splenocytes were cultured at 2.5×10$^5$ cells/ml in RPMI supplemented with 10% FCS for 24 hours in the presence of the indicated TLR ligands (final concentration 5-20 ug/ml). Soluble factors of human origin secreted into the culture supernatant were detected and quantitated using Luminex technology.

6.2 Results

Flk2-deficient mice were initially described on a C57BL/6 background (Mackarehtschian et al., 1995, Immunity 3:147-61). A PCR based screening assay was established to detect the WT and KO Flk2 alleles. Once established, backcrossing of the Flk2 mutant allele onto the Balb/c background was performed. Over 7 backcross generations were performed. The Flk2 mutant mice were then crossed with Rag2$^{-/-}$γc$^{-/-}$ Balb/c mice to generate a Rag2$^{-/-}$γc$^{-/-}$Flk2$^{-/-}$ mutant mice on the Balb/c background (FIG. 1).

The Rag2$^{-/-}$γc$^{-/-}$Flk2$^{-/-}$ strain was tested to determine whether they had the desired characteristics by injecting these mice (and Rag2$^{-/-}$γc$^{-/-}$ mice as controls) with B16 melanoma cells that constitutively secrete mouse Flk2 ligand. Tumor-bearing mice were analyzed for effects on the dendritic cell compartment. Mice with a functional Flk2 receptor had largely expanded DC in spleen and bone marrow. The Rag2$^{-/-}$γc$^{-/-}$Flk2$^{-/-}$ mice had no changes in their DC compartments compared to non-tumor injected mice. These results (FIG. 2) demonstrate that residual mouse DC in Rag2$^{-/-}$γc$^{-/-}$Flk2$^{-/-}$ mice can not respond to exogenous Flk2 ligand.

Figure 3:
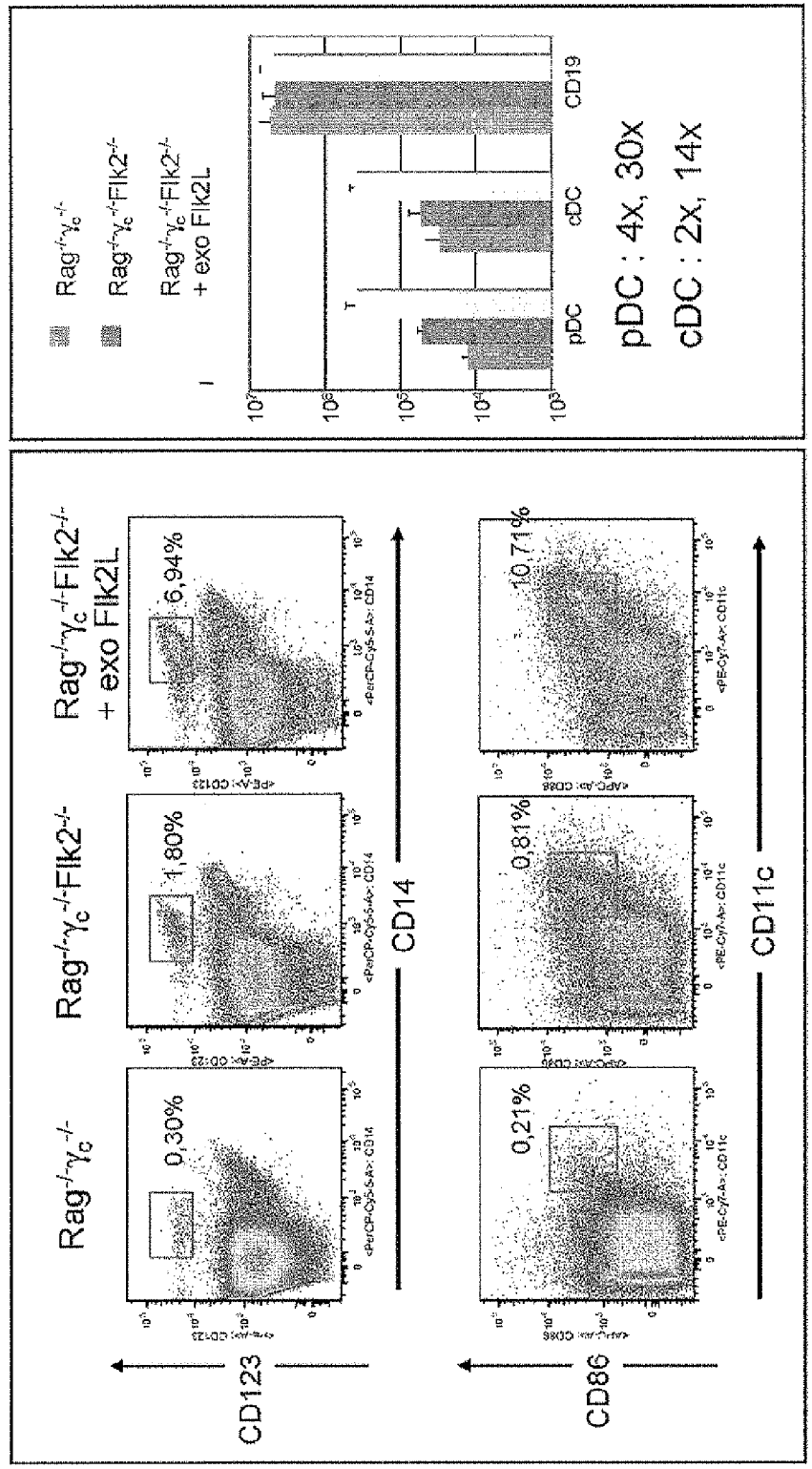

The procedure previously described by Huntington et al. (2009, Journal of Experimental Medicine 206:25-34) was used to reconstitute the human immune system in Rag2$^{-/-}$γc$^{-/-}$Flk2$^{-/-}$ mice. Human B and T cell development was similar to that previously reported. HIS mice made in the Rag2$^{-/-}$γc$^{-/-}$Flk2$^{-/-}$ strain were injected with Flk2L (5 µg/mouse; 3 times per week for 2 weeks) and analyzed at 8 weeks of age. These mice are referred to as DC boosted HIS mice. Strong expansion of the human DC compartment was observed in DC boosted HIS mice (FIG. 3). Splenocytes from DC-boosted HIS mice were isolated and stimulated in vitro using a panel of ligands that activate human and/or mouse DC. Soluble factors secreted by these cultured cells were then assayed for human interferon-α and human IL-12. Only DC-boosted HIS mice harbored human DC with the capacity to appropriately produce human interferon-α and human IL-12 following stimulation with TLR ligands (FIG. 4). In DC-boosted HIS mice, development of human NK cells was also improved (FIG. 5) suggesting that increased availability of human DC-derived cytokines (for example, IL-15) could also impact on the homeostasis of human NK cells in this HIS mouse model.

What is claimed is:

1. A mouse deficient for Rag2 and/or Rag1, interleukin-2 receptor gamma chain and Flk2 said mouse having 5 µg of Flk-2L administered into the mouse for three times per week for two weeks, said mouse further comprising: (i) a functional xenogenic immune system comprising xenogenic hematopoietic progenitor cells; and (ii) exogenous Flk-2L.

2. A method for producing a chimeric mouse having a functional xenogenic immune system, comprising the steps of:
  (i) transplanting xenogenic hematopoietic progenitor cells into a mouse deficient for Rag2 and/or Rag1, interleukin-2 receptor gamma chain and Flk2; and
  (ii) administering 5 µg of Flk-2L for three times per week for two weeks into the mouse deficient for Rag2 and/or Rag1, interleukin-2 receptor gamma chain and Flk2, thereby producing said chimeric mouse having a functional xenogenic immune system.

3. The method according to claim 2, wherein the xenogenic hematopoietic progenitor cells are human hematopoietic progenitor cells.

4. The mouse according to claim 1, wherein the xenogenic hematopoietic progenitor cells are human hematopoietic progenitor cells.

5. The mouse according to claim 1, wherein the Flk-2L is human Flk-2L.

6. The method according to claim 2, wherein the Flk-2L is human Flk-2L.

7. The method according to claim 2, wherein the Flk-2L is administered through the implantation of cells other than xenogenic hematopoietic progenitor cells that express Flk-2L.

8. The method according to claim 7, wherein the cells that express Flk-2L are genetically engineered cells.

9. The mouse of according to claim 1, wherein said mouse has a Balb/c background.

10. The method according to claim 2, wherein said mouse deficient for Rag2 and/or Rag1, interleukin-2 receptor gamma chain and Flk2 has a Balb/c background.

\* \* \* \* \*